(12) United States Patent
Furukawa

(10) Patent No.: US 10,018,616 B2
(45) Date of Patent: Jul. 10, 2018

(54) CHARGING DEVICE FOR BIOLOGICAL INFORMATION MEASUREMENT DEVICE AND BIOLOGICAL INFORMATION MEASUREMENT DEVICE CHARGED USING SAME

(71) Applicant: PHC Holdings Corporation, Minato-ku, Tokyo (JP)

(72) Inventor: Tatsuhiko Furukawa, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 0 days.

(21) Appl. No.: 15/719,457

(22) Filed: Sep. 28, 2017

(65) Prior Publication Data
US 2018/0017544 A1 Jan. 18, 2018

Related U.S. Application Data

(60) Continuation of application No. 15/436,866, filed on Feb. 20, 2017, now Pat. No. 9,804,147, which is a
(Continued)

(30) Foreign Application Priority Data

Mar. 12, 2012 (JP) .................................. 2012-054162
Sep. 7, 2012 (JP) .................................. 2012-196947

(51) Int. Cl.
*G08B 21/00* (2006.01)
*G01N 33/487* (2006.01)
*H02J 7/02* (2016.01)

(52) U.S. Cl.
CPC ........ *G01N 33/48785* (2013.01); *H02J 7/025* (2013.01)

(58) Field of Classification Search
CPC ........................ G01N 33/48785; H02J 7/025
See application file for complete search history.

(56) References Cited

U.S. PATENT DOCUMENTS

2002/0177793 A1 11/2002 Sherman et al.
2002/0193703 A1 12/2002 Sato et al.
(Continued)

FOREIGN PATENT DOCUMENTS

JP S63-260542 A 10/1988
JP 2003-000551 A 1/2003
(Continued)

OTHER PUBLICATIONS

The Search Report from International Application No. PCT/JP2013/001383 dated May 14, 2013.
The Office Action from the corresponding Japanese Patent Application No. 2015-098269 dated Mar. 15, 2016.
The Notice of Allowance from the corresponding Japanese Patent Application No. 2015-098269 dated Aug. 30, 2016.
The Notice of Allowance from the co-pending U.S. Appl. No. 14/374,218 dated Dec. 2, 2016.
The Office Action from the corresponding Japanese Patent Application No. 2016-178510 dated Jul. 18, 2017.

*Primary Examiner* — Omeed Alizada
(74) *Attorney, Agent, or Firm* — Shinjyu Global IP

(57) ABSTRACT

Certain implementations have a main body case having a contact face of a biological information measurement device on its surface, and a first non-contact charging portion composed of a charging coil disposed opposite the contact face with the biological information measurement device inside the main body case. In addition, some may have a controller that is connected to the first non-contact charging portion, and a display section that is connected to the controller. Upon completion of the charging of the biological information measurement device via the first non-contact charging portion, the controller connected to the display section may display on the display section that the biological information measurement device will be incapable of measurement for a specific length of time.

3 Claims, 7 Drawing Sheets

Related U.S. Application Data division of application No. 14/374,218, filed as application No. PCT/JP2013/001383 on Mar. 6, 2013, now Pat. No. 9,614,393.

(56) References Cited

U.S. PATENT DOCUMENTS

| | | |
|---|---|---|
| 2004/0068230 A1 | 4/2004 | Estes et al. |
| 2006/0173367 A1 | 8/2006 | Stuart et al. |
| 2010/0268475 A1 | 10/2010 | Kusumoto |
| 2011/0167250 A1 | 7/2011 | Dicks et al. |
| 2011/0179405 A1 | 7/2011 | Dicks et al. |
| 2012/0150047 A1 | 6/2012 | Terumoto et al. |
| 2012/0197347 A1* | 8/2012 | Olson ................ A61N 1/37217 607/60 |

FOREIGN PATENT DOCUMENTS

| | | |
|---|---|---|
| JP | 2003-207445 A | 7/2003 |
| JP | 2003-255069 A | 9/2003 |
| JP | 2009-022102 A | 1/2009 |
| JP | 2010-057694 A | 3/2010 |
| JP | 2010-136594 A | 6/2010 |
| JP | 2012-120773 A | 6/2012 |
| WO | 2004/084624 A1 | 10/2004 |
| WO | 2009/119116 A1 | 10/2009 |

* cited by examiner

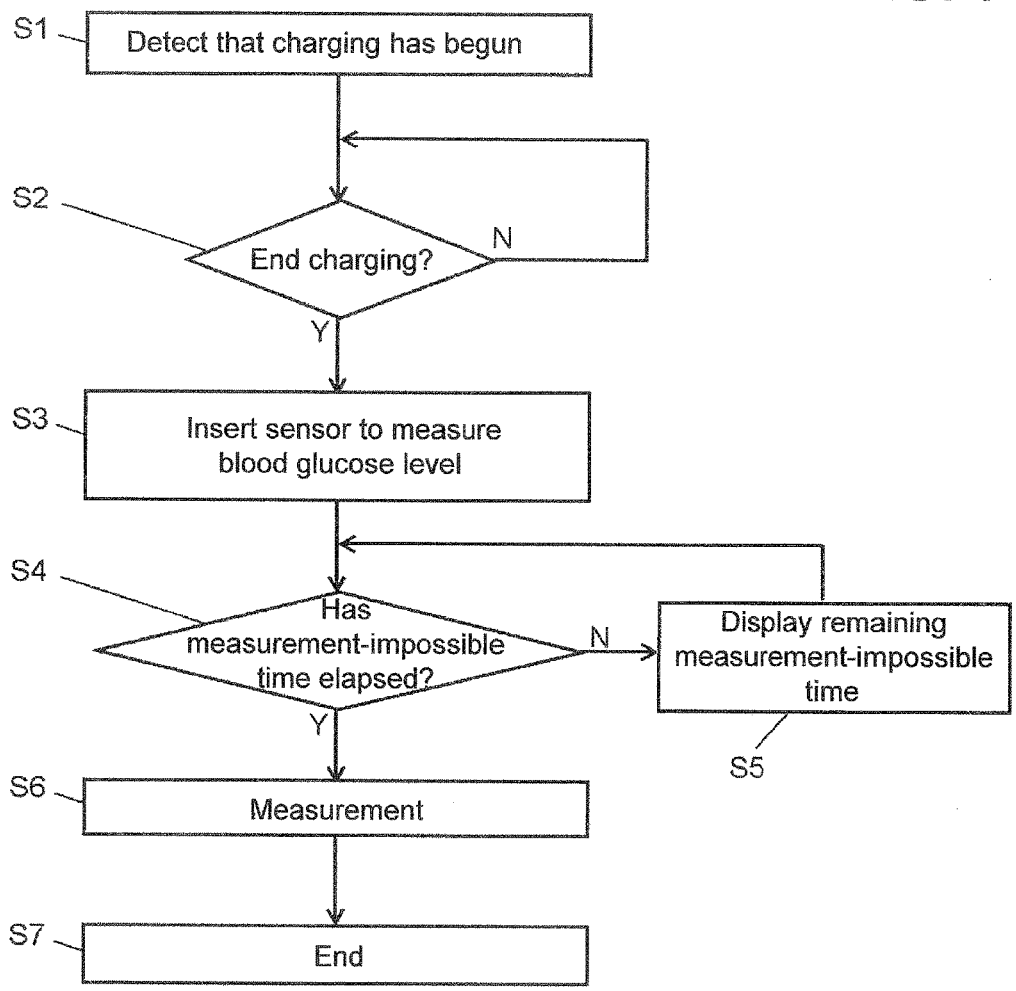

CHARGING DEVICE FOR BIOLOGICAL INFORMATION MEASUREMENT DEVICE AND BIOLOGICAL INFORMATION MEASUREMENT DEVICE CHARGED USING SAME

PRIORITY

This application is a continuation application of U.S. application Ser. No. 15/436,866 filed on Feb. 20, 2017 which is a divisional application of U.S. application Ser. No. 14/374,218 filed on Jul. 23, 2014 which claims priority to International Application PCT/JP2013/001383, with an international filing date of Mar. 6, 2013, which claims priority to Japanese Patent Application No. 2012-054162 filed on Mar. 12, 2012 and Japanese Patent Application No. 2012-196947 filed on Sep. 7, 2012. The entire disclosures of U.S. application Ser. Nos. 15/436,866, 14/374,218, International Application PCT/JP2013/001383, Japanese Patent Application No. 2012-054162, and Japanese Patent Application No. 2012-196947 are hereby incorporated herein by reference.

TECHNICAL FIELD

The present invention relates to a charging device for a biological information measurement device, and to a biological information measurement device that is charged by said charging device, and can be put to use when biological information (such as a blood glucose level) is measured from blood, for example.

BACKGROUND

A conventional charging device for a biological information measurement device of this type had a first main body case with a biological information measurement device contact face on its surface, a charger inside this first main body case, a controller connected to this charger, and a display section connected to this controller (see Patent Literature 1: Japanese Laid-Open Patent Application 2010-136594, for example).

If the battery of the biological information measurement device ran low, the biological information measurement device was brought into contact with the contact face of the charging device for a biological information measurement device, and the biological information measurement device was charged.

With the conventional configuration discussed above, however, a problem was that measurement could not be executed properly after charging.

Specifically, when the battery inside the biological information measurement device was charged, heat was generated by the battery, which raised the temperature inside the biological information measurement device. For example, when the biological information measurement device was one that measured blood glucose levels, temperature correction for the blood glucose level was performed by using the temperature inside the first main body case of the biological information measurement device, but proper temperature correction could not be performed in a state in which the temperature inside the first main body case had risen, and as a result the proper measurement could not be performed.

In view of this, it is an object of the present invention to allow proper measurement to be performed with a biological information measurement device.

SUMMARY

The present invention comprises a first main body case having a contact face of the biological information measurement device on its surface, a first non-contact charging portion disposed inside the first main body case and opposite the contact face, a first controller that is connected to the first non-contact charging portion, and a first display section that is connected to the first controller. The first controller displays on the first display section that the biological information measurement device will be incapable of measurement for a specific length of time after the end of charging of the biological information measurement device.

With the present invention, since the biological information measurement device is incapable of measurement for a specific length of time, that is, until the temperature inside the biological information measurement device naturally cools to the temperature outside the biological information measurement device, the user can recognize that the biological information measurement device is incapable of measurement.

When the biological information measurement device is used after this display has disappeared, the temperature inside the biological information measurement device has by that time naturally cooled to the same temperature as that outside the biological information measurement device, so the proper temperature correction can be accomplished.

As a result, the proper measurement can be carried out.

BRIEF DESCRIPTION OF DRAWINGS

FIG. 6 shows the display on the display section of the charging device for a biological information measurement device in the first embodiment of the present invention;

FIG. 7 is an operational flowchart of the biological information measurement device in the first embodiment of the present invention;

FIG. 8 shows the display on the display section of the biological information measurement device in the first embodiment of the present invention;

DETAILED DESCRIPTION

The charging device for a biological information measurement device, and the biological information measurement device charged by this charging device, in the first embodiment of the present invention will now be described through reference to the drawings. It will be apparent to those skilled in the art from this disclosure that the following descriptions of the embodiment is provided for illustration only and not for the purpose of limiting the invention as defined by the appended claims and their equivalents.

First Embodiment

Figure 1:
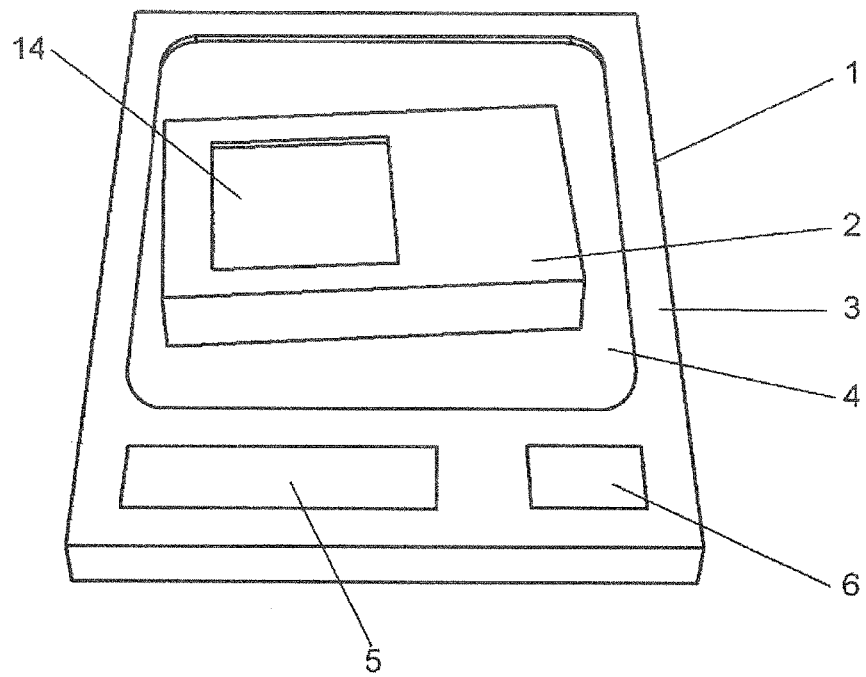
FIG. 1 is an oblique view of the usage state of the charging device for a biological information measurement device in a first embodiment of the present invention.

As shown in FIG. 1, the biological information measurement device charging device 1 charges, for example, a biological information measurement device 2 that measures blood glucose levels from blood, which is an example of biological information.

The biological information measurement device charging device 1 has a flat main body case (first main body case) 3 whose upper face is quadrangular, and a contact face 4 of the biological information measurement device 2 is provided over a wide area of this upper face. This contact face 4 is formed by a substantially square recess, and the bottom of this recess is flat. That is, when the biological information measurement device 2 is placed on the flat part of the recess forming this contact face 4, the biological information measurement device 2 is charged. This charging is non-contact charging that makes use of a magnetic flux, which is used in the charging of household electric shavers and so forth.

The contact face 4 is formed larger than the main body case 3 of the biological information measurement device 2, which affords some room for error in the placement of the biological information measurement device 2.

A display section (first display section) 5 and a charging start key 6 are provided around the contact face 4 on the upper face of the biological information measurement device charging device 1.

Figure 2:
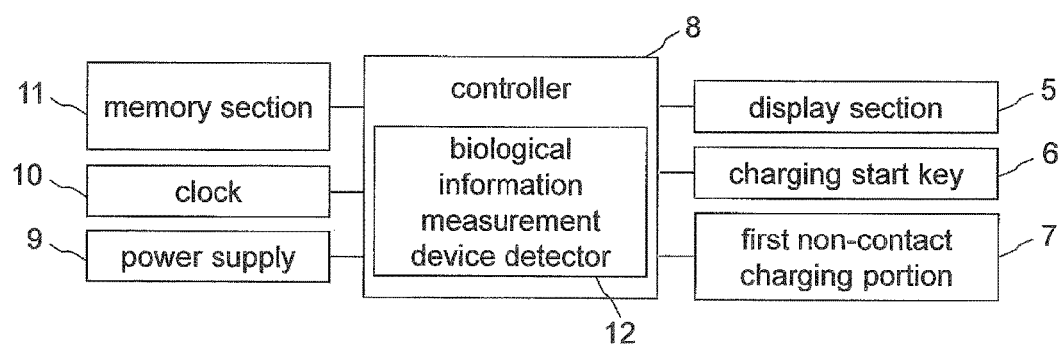
FIG. 2 is a block diagram of the charging device for a biological information measurement device in the first embodiment of the present invention.

FIG. 2 is a control block diagram of the biological information measurement device charging device 1.

A first non-contact charging portion 7 composed of a charging coil is disposed at a position opposite the contact face 4 in FIG. 1 on the inside of the main body case 3, and is connected to a controller (first controller) 8. This controller 8 is also connected to the display section 5 and the charging start key 6, as well as a power supply 9, a clock 10, and a memory section 11. Also, a biological information measurement device detector 12 that detects that the biological information measurement device 2 has been set on the contact face 4 is provided inside the controller 8.

Figure 3:
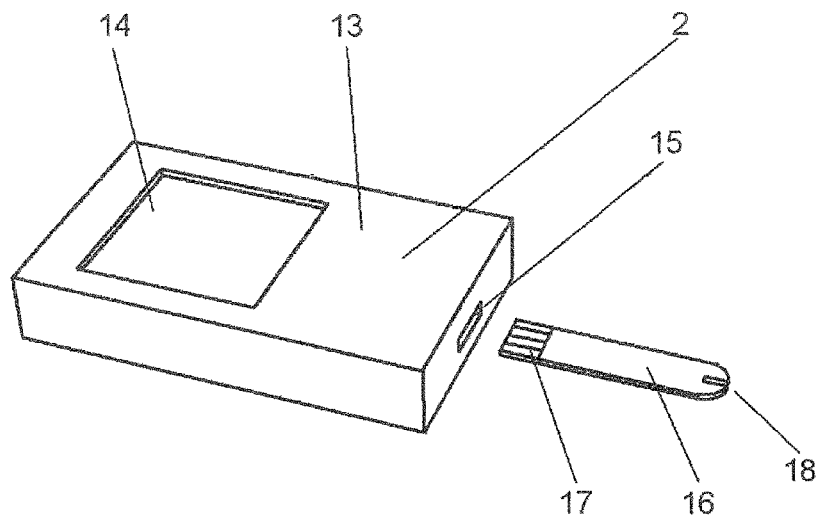
FIG. 3 is an oblique view of the biological information measurement device in the first embodiment of the present invention.

The biological information measurement device 2 that is charged by this biological information measurement device charging device 1 will be described through reference to FIGS. 3 and 4.

The biological information measurement device 2 has a cuboid main body case (second main body case) 13, and a display section (second display section) 14 is provided on the upper face of this main body case 13. A sensor mounting portion 15 is provided on the distal end side of this main body case 13. A connector terminal 17 of a flat, rectangular blood glucose level sensor 16 is mounted to this sensor mounting portion 15, and when blood is deposited on a deposition portion 18, the blood glucose level is measured by the measurement section 19 in FIG. 4. The blood glucose level is temperature-corrected with the temperature of the temperature sensor 20 in FIG. 4. This temperature-corrected blood glucose level is displayed on the display section 14 by a controller (second controller) 21.

Figure 4:
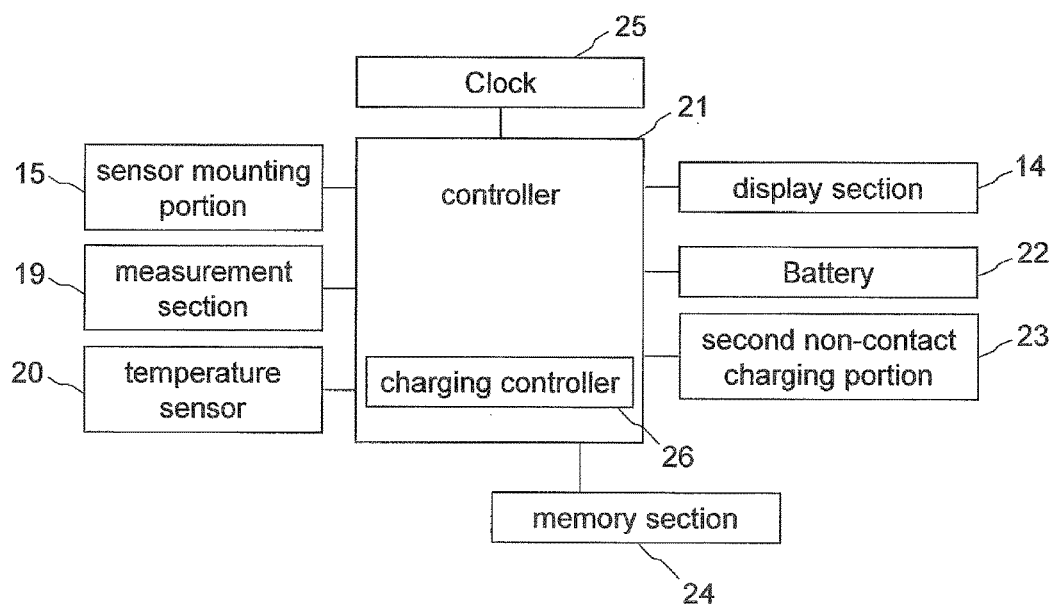
FIG. 4 is a block diagram of the biological information measurement device in the first embodiment of the present invention.

As shown in FIG. 4, the sensor mounting portion 15 of the biological information measurement device 2 is connected to the measurement section 19 inside the biological information measurement device 2, and this measurement section 19 is connected to the controller 21. Inside the biological information measurement device 2, the controller 21 is connected to the display section 14, the temperature sensor 20, a rechargeable battery 22, a second non-contact charging portion 23 composed of a charging coil, a memory section 24, and a clock 25. Also, a charging controller 26 that controls the rechargeable battery 22 and the second non-contact charging portion 23 during the charging of the rechargeable battery 22 is provided inside the controller 21.

As performance has improved in recent years, the size of the display section 14 used in the biological information measurement device 2 has increased, and this has led to higher power consumption. Accordingly, the rechargeable battery 22 is provided inside the main body case 13, and is suitably charged when the capacity of the rechargeable battery 22 runs low, thereby ensuring that the device has power.

The charging of the biological information measurement device 2 by the biological information measurement device charging device 1 is performed by non-contact charging by the first non-contact charging portion 7 at a drive frequency of 145 kHz, for example.

The operation during charging of the biological information measurement device charging device 1 in the above configuration will now be described through reference to the flowchart in FIG. 5.

As shown in FIG. 1, when the user places the biological information measurement device 2 on the contact face 4 of the biological information measurement device charging device 1, the biological information measurement device charging device 1 starts charging the biological information measurement device 2.

First, the controller 8 of the biological information measurement device charging device 1 starts intermittent communication with the biological information measurement device detector 12 in order to confirm that the biological information measurement device 2 has been placed on the contact face 4. More specifically, the biological information measurement device detector 12 starts to send a trickle current intermittently, at specific intervals, to the first non-contact charging portion 7 (step S1 in FIG. 5).

When the user places the biological information measurement device 2 on the contact face 4 in this state, the first non-contact charging portion 7 inside the biological information measurement device charging device 1 reacts to a reflection signal from the second non-contact charging portion 23 inside the biological information measurement device 2, and the impedance thereof changes. Accordingly, the amount of current flowing to the first non-contact charging portion 7 changes. When the biological information measurement device detector 12 detects this change, the controller 8 confirms that the biological information measurement device 2 has been placed on the contact face 4 (step S2 in FIG. 5).

After this confirmation, charging of the biological information measurement device 2 begins.

When this charging begins, heat is generated by the rechargeable battery 22, which ends up raising the temperature inside the biological information measurement device 2. Upon completion of the charging, this elevated temperature is measured by the temperature sensor 20 inside the biological information measurement device 2, and if temperature correction is done at this measured temperature, the proper temperature correction cannot be performed, and as a result the proper measurement cannot be accomplished.

In view of this, in this embodiment the biological information measurement device 2 is provided with a measurement-impossible time, during which it is incapable of measurement, after the end of charging. The biological information measurement device 2 is then allowed to cool naturally within this measurement-impossible time. The display apprises the user, prior to the start of charging, that the biological information measurement device 2 will be incapable of measurement for a time after the end of charging.

More specifically, as shown in FIG. 6, the controller 8 displays "No measurement right away?" on the display section 5 of the biological information measurement device charging device 1 before the start of charging, and prompts the user to confirm the end of measurement with the biological information measurement device 2.

Figure 5:
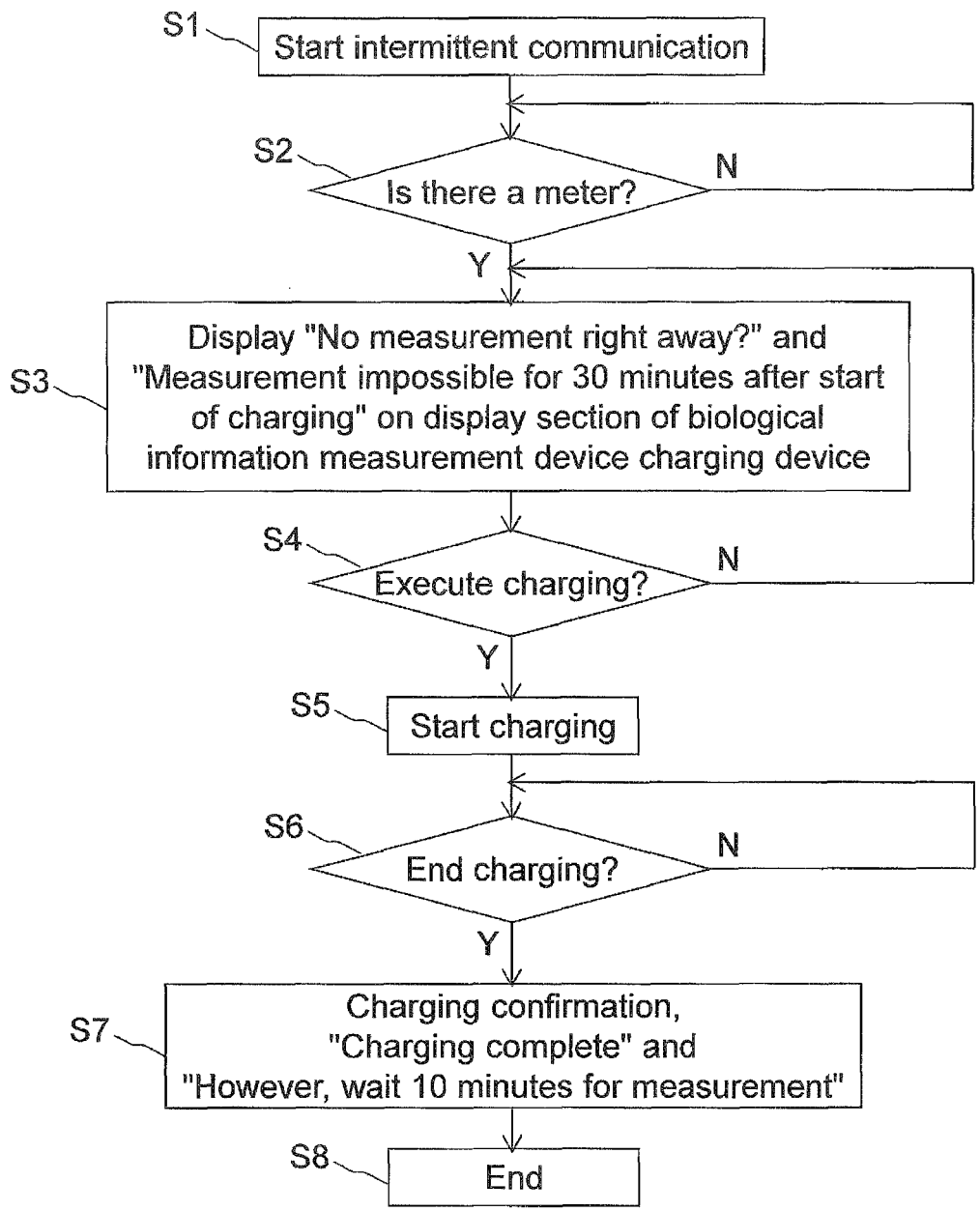
FIG. 5 is an operational flowchart of the charging device for a biological information measurement device in the first embodiment of the present invention.

Next, the controller 8 displays "Measurement impossible for 30 minutes after start of charging" and the measurement-impossible time (30 minutes) on the display section 5 of the biological information measurement device charging device 1, notifies the user that the biological information measurement device 2 will be incapable of measurement for a time after the end of charging (step S3 in FIG. 5). This measurement-impossible time (30 minutes) is a pre-calculated maximum measurement-impossible time, and is stored in the memory section 11 of the biological information measurement device charging device 1.

These two displays alert the user to the fact that the biological information measurement device 2 cannot be used for a time after the start and end of charging of the biological information measurement device 2, and allow the user to measure a blood glucose level if measurement by the biological information measurement device 2 is not yet finished. These two displays continue until the user presses the charging start key 6 of the biological information measurement device charging device 1 (steps S3 and S4 in FIG. 5 are repeated).

When the user presses the charging start key 6 of the biological information measurement device charging device 1, charging of the biological information measurement device 2 begins. When charging begins, the biological information measurement device 2 enters a state of being incapable of measurement for a specific length of time (this will be discussed in detail below).

At the start of this charging, the controller 8 of the biological information measurement device charging device 1 displays on the display section 5 that the biological information measurement device 2 will be incapable of measurement for a specific length of time. More specifically, the controller 8 displays "Measurement impossible for now" on the display section 5 of the biological information measurement device charging device 1. The controller 8 also acquires the charging start time with the clock 10 and stores it in the memory section 11.

When charging begins, the controller 8 of the biological information measurement device charging device 1 charges the biological information measurement device 2 by continuously sending a specific amount of current to the first non-contact charging portion 7, which is composed of a charging coil (step S5 in FIG. 5).

This charging is performed by non-contact charging that makes use of a magnetic flux, which is used in the charging of household electric shavers and so forth. That is, a magnetic flux is generated in the first non-contact charging portion 7 by sending current to the first non-contact charging portion 7, which is composed of a charging coil. An electromotive force is generated in the second non-contact charging portion 23 (composed of a charging coil) of the biological information measurement device 2, using this magnetic flux as a medium. This electromotive force of the second non-contact charging portion 23 is controlled by the charging controller 26 of the biological information measurement device 2, and the rechargeable battery 22 is charged. The charging of the rechargeable battery 22 continues in this state, and is ended after a specific amount of time has elapsed (such as after 5 minutes) (step S6 in FIG. 5).

When the charging is finished, the controller 8 of the biological information measurement device charging device 1 calculates the remaining measurement-impossible time.

More specifically, the controller 8 acquires the charging completion time from the clock 10, compares it with the charging start time in the memory section 11, and finds the charging duration. The cooling duration (the remaining measurement-impossible time) is calculated from this charging duration.

The charging here lasted for 5 minutes, so the measurement-impossible time is set at 10 minutes, which is two times the charging duration (the factor for calculating the measurement-impossible time), for example.

The factor for calculating the measurement-impossible time here was two times the charging duration, but this calculation factor may be suitably determined according to the configuration of the biological information measurement device 2. The calculation factor thus determined is stored ahead of time in the memory section 11 of the biological information measurement device charging device 1.

The controller 8 of the biological information measurement device charging device 1 displays the calculated measurement-impossible time by displaying "Charging complete" and "However, wait 10 minutes for measurement" on the display section 5 of the biological information measurement device charging device 1 (step S7 in FIG. 5).

This display allows the user to accurately ascertain the remaining measurement-impossible time.

Within this measurement-impossible time, the temperature inside the biological information measurement device 2 naturally cools to the temperature outside the biological information measurement device 2, and therefore after the measurement-impossible time has elapsed, the proper temperature correction can be performed. As a result, the proper measurement can be performed.

After this, the controller 8 of the biological information measurement device charging device 1 ends the series of charging processing (step S8 in FIG. 5).

The operation of the biological information measurement device 2 during charging will now be described through reference to the operational flowchart in FIG. 7.

The controller 21 of the biological information measurement device 2 uses the charging controller 26 to detect that electricity has begun to flow to the second non-contact charging portion 23 (composed of a charging coil), and the controller 21 thereby detects that charging has begun (step S1 in FIG. 7).

At the start of charging, the controller 21 displays the measurement-impossible time and "No measurement for 30 minutes after the start of charging" on the display section 14 of the biological information measurement device 2. How long this measurement-impossible time is displayed on the display section 14 is a pre-calculated maximum measurement-impossible time, and is stored in the memory section 24 of the biological information measurement device 2.

Next, the controller 21 of the biological information measurement device 2 renders measurement by the measurement section 19 impossible during the measurement-impossible time.

At this point the controller 21 uses the timer function of the clock 25 to start counting up the charging duration. More specifically, the count on the timer of the clock 25 is increased to measure the charging duration.

After this, the charging controller 26 is used to start charging the rechargeable battery 22. The charging controller 26 charges the rechargeable battery 22 with current flowing to the second non-contact charging portion 23 (composed of a charging coil), and the charging is continued until the voltage of the rechargeable battery 22 reaches a specific level (step S2 in FIG. 7 is repeated).

When the charging is finished, the controller 21 calculates the accurate measurement-impossible time. More specifically, the count-up of the timer of the clock 25 is stopped, the charging duration is calculated from this count-up value, and the cooling duration (the remaining measurement-impossible time) is calculated from this charging duration.

The charging here lasted for 5 minutes, so the measurement-impossible time is set at 10 minutes, which is two times the charging duration (the factor for calculating the measurement-impossible time), for example.

The factor for calculating the measurement-impossible time here was two times the charging duration, but this calculation factor may be suitably determined according to the configuration of the biological information measurement device 2. The calculation factor thus determined is stored ahead of time in the memory section 24 of the biological information measurement device 2.

As shown in FIG. 8, the controller 21 of the biological information measurement device 2 displays the measurement-impossible time and "No measurement for another 10 minutes" on the display section 14 of the biological information measurement device 2. This display allows the user to accurately ascertain the remaining measurement-impossible time. This measurement-impossible time is stored in the memory section 24. The time function of the clock 25 is then used to start counting down the measurement-impossible time, and the count is updated until the measurement-impossible time of the memory section 24 reaches zero.

After this, the user lifts the biological information measurement device 2 up from the biological information measurement device charging device 1, mounts the blood glucose level sensor 16 to the sensor mounting portion 15 of the biological information measurement device 2, and electrically connects the connector terminal 17 to the measurement section 19 (step S3 in FIG. 7). Also, the controller 21 of the biological information measurement device 2 determines whether or not the measurement-impossible time of the memory section 24 has elapsed. More specifically, it is confirmed whether or not the measurement-impossible time of the memory section 24 has reached zero (step S4 in FIG. 7).

If the measurement-impossible time has not yet elapsed, that is, if the measurement-impossible time is not zero, the controller 21 takes the measurement-impossible time out of the memory section 24 and displays it on the display section 14 (step S5 in FIG. 7).

An example will be described. Let us assume that charging of the biological information measurement device 2 is started before breakfast, and charging is complete 5 minutes later. The remaining measurement-impossible time at this point is 10 minutes, since the charging lasted 5 minutes. If the user connects the blood glucose level sensor 16 to the biological information measurement device 2 at 5 minutes after this point, the measurement-impossible state and "No measurement for another 5 minutes" are displayed on the display section 14 of the biological information measurement device 2.

The user looks at this display and can ascertain that the biological information measurement device 2 is still in a state in which measurement is impossible.

Meanwhile, after the measurement-impossible time has elapsed, a display of "Measurement is possible" is given on the display section 14 of the biological information measurement device 2 by the controller 21 to notify the user that measurement is now possible. The user starts measuring the blood glucose level, this value is displayed on the display section 14 (step S6 in FIG. 7), and the measurement is concluded (step S7 in FIG. 7).

Specifically, as described above, in this embodiment the biological information measurement device 2 is in a state in which measurement is impossible for a specific length of time after the end of charging by the biological information measurement device charging device 1.

At this point, the display section 5 of the biological information measurement device charging device 1 displays that the biological information measurement device 2 will be incapable of measurement for a specific length of time (that is, until the temperature inside the biological information measurement device 2 naturally cools to the temperature outside the biological information measurement device 2), so the user can recognize that measurement is impossible with the biological information measurement device 2.

When the biological information measurement device 2 is used after this display has disappeared, since the temperature inside the biological information measurement device 2 at that point has naturally cooled to the same temperature as the one outside the biological information measurement device 2, the proper temperature correction can be performed.

As a result, the proper measurement can be carried out.

Thus making measurement with the biological information measurement device 2 impossible for a specific length of time after charging would at first seem to make the device less convenient, but in this embodiment, as discussed above, a message indicating that the biological information measurement device 2 will not be capable of measurement for a while after the start of charging is displayed ahead of time, and the user is prompted to perform measurement.

When a blood glucose level is measured by an individual, once a measurement is taken, it is almost never the case that another measurement will be taken again in a short period (such as between measurement before breakfast and measurement before lunch). Accordingly, if measurement is performed before the start of charging, there will be no practical problem even though there is a measurement-impossible time after charging.

Also, in this embodiment, as discussed above, all the user has to do to perform automatic non-contact charging is to place the biological information measurement device 2 on the contact face 4, which makes the device very convenient to use and allows daily charging to be accomplished simply.

Since daily charging can thus be carried out simply, in this embodiment the rechargeable battery 22 of the biological information measurement device 2 can be smaller. Therefore, the biological information measurement device 2 can be more lightweight and easier to handle. Also, because the rechargeable battery 22 is smaller, a single charge will take less time, and this also makes handling easier.

When the biological information measurement device 2 is not being used, the controller 21 goes into what is known as sleep mode to reduce drain of the battery 22.

Second Embodiment

The biological information measurement device charging device, and the biological information measurement device charged by the same, in a second embodiment of the present invention will now be described through reference to FIGS. 9 to 12. The constituent elements that are the same as in the first embodiment will be numbered the same and not described again, and some will not be depicted.

When the biological information measurement device 2 is not being used, as discussed above, for example, the controller 21 goes into sleep mode to reduce drain of the battery 22, but there will still be a slight drain on the battery.

Accordingly, if the biological information measurement device 2 is not used for an extended period, such as when a long time elapses between the time when the biological information measurement device 2 is shipped from the factory until it is given to the user, there is the risk that the battery 22 will be drained.

In particular, if the time display on the clock 25 inside the biological information measurement device 2 should be off due to drain on the battery 22, then it may be that the precise measurement time cannot be recorded along with the blood glucose level when a blood glucose level is measured, and a health evaluation using a number of blood glucose levels cannot be performed.

In view of this, in the second embodiment of the present invention, the clock 25 of the biological information measurement device 2 can be set to the precise time.

Figure 9:
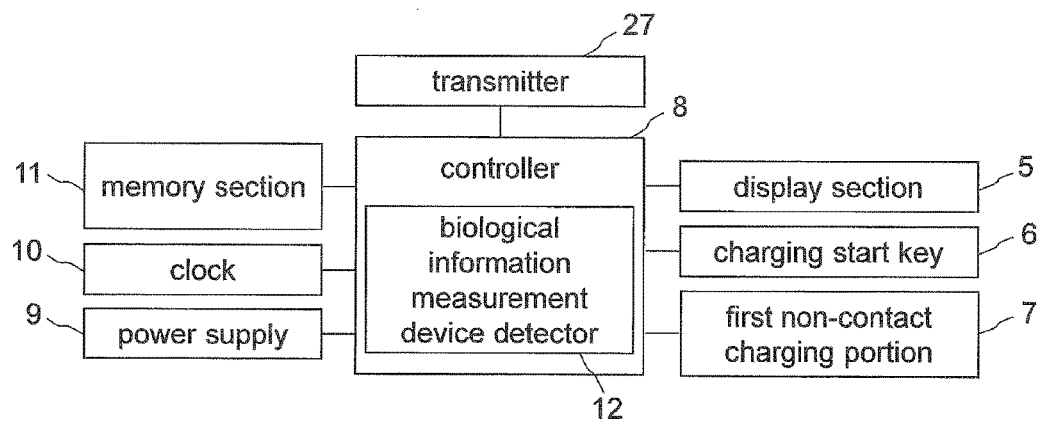
FIG. 9 is a block diagram of the charging device for a biological information measurement device in a second embodiment of the present invention.

Accordingly, as shown in FIG. 9, with the biological information measurement device charging device 1 in this embodiment, the controller 8 is connected to the clock 10 and a transmitter 27 that sends time information from this clock 10 by radio waves.

Figure 10:
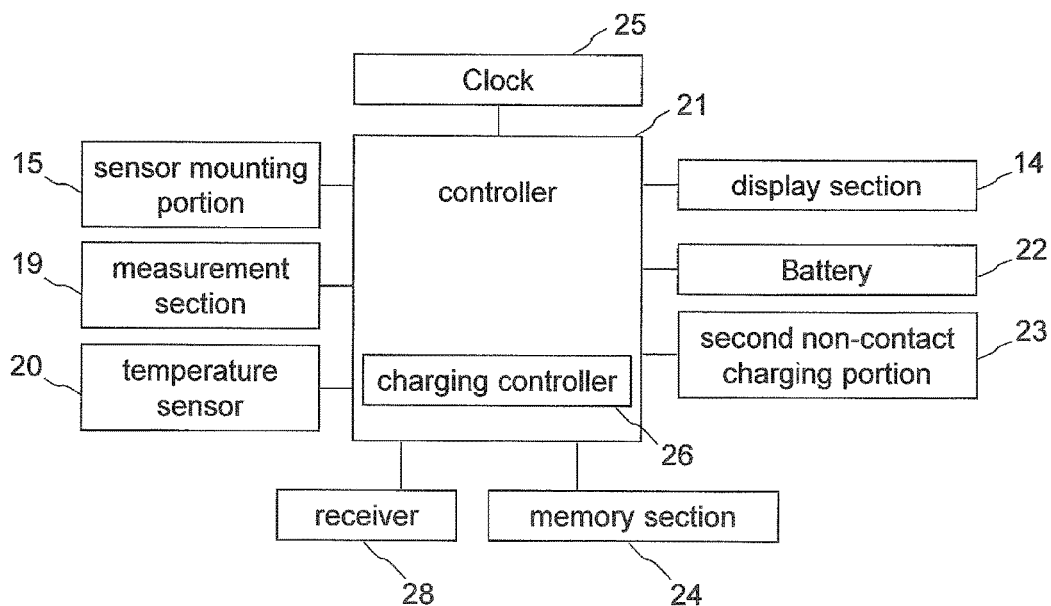
FIG. 10 is a block diagram of the biological information measurement device in the second embodiment of the present invention.

As shown in FIG. 10, a receiver 28 that receives by radio waves time information sent out by the transmitter 27 of the biological information measurement device charging device 1 is connected to the controller 21 of the biological information measurement device 2.

Specifically, when the biological information measurement device 2 is placed on the biological information measurement device charging device 1, the biological information measurement device 2 is charged, and during this charging, time information from the clock 10 of the biological information measurement device charging device 1 can be sent to the clock 25 of the biological information measurement device 2 via the transmitter 27 and the receiver 28.

As a result, the clock 25 of the biological information measurement device 2 can be set to the precise time.

This time setting will now be described in detail.

First, preparation for charging with the biological information measurement device charging device 1 will be described.

In this embodiment, the clock 10 of the biological information measurement device charging device 1 shown in FIG. 9 is constituted by a radio-controlled clock that receives digital signals transmitted from a standard radio wave broadcast station and automatically sets the time.

When the user plugs the biological information measurement device charging device 1 into a household outlet (not shown), the power is switched on to the biological information measurement device charging device 1, and the biological information measurement device charging device 1 is started up. The clock 10 then receives a digital signal transmitted from the standard radio wave broadcast station, allowing the time to be automatically set on the clock 10.

If the time has not been set on the biological information measurement device charging device 1, the controller 8 of the biological information measurement device charging device 1 will deactivate operation of the charging start key 6. When the time setting of the biological information measurement device charging device 1 is then finished, the controller 8 activates the operation of the charging start key 6, and charging preparation is concluded.

Next, the operation of the biological information measurement device charging device 1 in time setting and charging of the biological information measurement device 2 will now be described through reference to the flowchart in FIG. 11.

Figure 11:
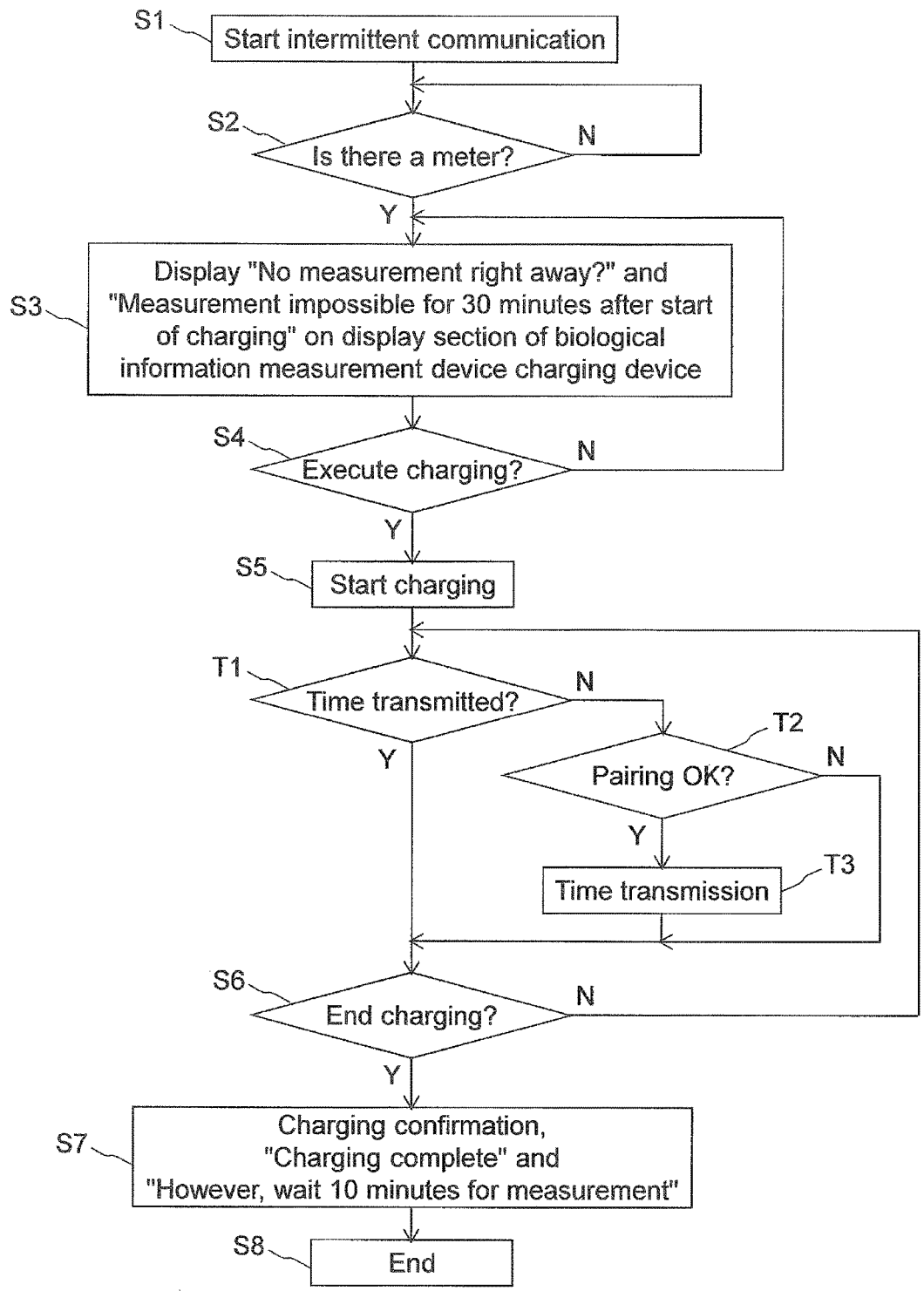
FIG. 11 is an operational flowchart of the charging device for a biological information measurement device in the second embodiment of the present invention.

In FIG. 11, steps T1 to T3 are inserted as time setting processing in between steps S5 and S6 in the charging flowchart of FIG. 5 (which shows the first embodiment).

When the user places the biological information measurement device 2 on the biological information measurement device charging device 1, the controller 8 of the biological information measurement device charging device 1 sequentially executes the processing of steps S1 to S4 in FIG. 11 in the same manner as the processing of steps S1 to S4 in FIG. 5 (discussed above), and the charging of step S5 in FIG. 11 is begun. This charging is non-contact charging, and is performed by the first non-contact charging portion 7 at a drive frequency of 145 kHz, for example.

When charging begins, the controller 8 of the biological information measurement device charging device 1 confirms whether or not time information has been sent from the clock 10 to the biological information measurement device 2 (step T1 in FIG. 9).

This confirmation is determined by whether or not communication end information (such as a communication end flag) has been stored in the memory section 11 of the biological information measurement device charging device 1. This communication end information is deleted in advance by the controller 8 in step S5 in FIG. 11 at the start of charging.

Immediately after the start of charging, the time information has not yet been sent from the clock 10 to the biological information measurement device 2, so there is no communication end information. In view of this, the controller 8 of the biological information measurement device charging device 1 pairs the transmitter 27 with the receiver 28 of the biological information measurement device 2 in order to send time information to the biological information measurement device 2, and confirms whether or not communication is possible (step T2 in FIG. 9).

This communication between the transmitter 27 and the receiver 28 is near field communication using RFID communication, for example.

Accordingly, the transmitter 27 of the biological information measurement device charging device 1 serves as a writer that transmits RFID information, and is controlled by the controller 8 to perform RFID communication by radio waves. The receiver 28 of the biological information measurement device 2 shown in FIG. 10 serves as a reader that reads the RFID information, and is controlled by the controller 21 to perform RFID communication by radio waves.

Once the pairing of the biological information measurement device charging device 1 and the biological information measurement device 2 is successful, the controller 8 of the biological information measurement device charging device 1 uses the transmitter 27 to send time information (current time) from the clock 10 of the biological information measurement device charging device 1 to the receiver 28 of the biological information measurement device 2. The biological information measurement device 2 performs the processing of steps T1 to T3 in FIG. 12 (discussed below), and sets the clock 25 to the precise time with the received time information.

At this point, the controller 8 of the biological information measurement device charging device 1 displays "Current time: 18:00:00" on the display section 5 of the biological information measurement device charging device 1, and notifies the user that the time setting of the biological information measurement device 2 is complete. After this, the display on the display section 5 of the biological information measurement device charging device 1 is updated to match the time, and after a specific length of time (such as 30 seconds), the display is switched to indicate that charging is in progress, such as "Charging."

This will be described in detail below, but a notice of the completion of time setting of the biological information measurement device 2 is also given on the display section 14 of the biological information measurement device 2, and the display on the display section 14 of the biological information measurement device 2 is updated to match the time.

Therefore, the user can recognize that the clocks of the biological information measurement device charging device 1 and the biological information measurement device 2 have been synchronized by comparing the updated information displayed on the biological information measurement device charging device 1 and the biological information measurement device 2.

The controller 8 of the biological information measurement device charging device 1 stores the communication end information in the memory section 11 (step T3 in FIG. 11).

The communication of time information is performed by the transmitter 27 at a transmission frequency of 13.56 MHz, for example.

With the biological information measurement device charging device 1 in this embodiment, since the drive frequency of the first non-contact charging portion 7 (eg, 145 kHz) is different from the transmission frequency of the transmitter 27 (eg, 13.56 MHz), the RFID communication is not hindered by charging, and as a result the clock 25 of the biological information measurement device 2 can be set during charging.

After this, step S6 in FIG. 11 is executed, and charging is continued.

In step S6 in FIG. 11, if charging has not yet finished, the flow returns to step T1 in FIG. 11. This time, the time information of the clock 10 is sent to the biological information measurement device 2 in step T3 in FIG. 11, so the flow returns to step S6 in FIG. 11 right away, and charging is continued.

In step T2 in FIG. 11, if pairing has failed, the controller 8 of the biological information measurement device charging device 1 executes step S6 in FIG. 11 and continues charging, while the flow returns to step T2 in FIG. 11 via step T1 in FIG. 11, and the transmitter 27 is again paired with the receiver 28 of the biological information measurement device 2.

When charging is finished, a transmission complete display (time setting complete display) is performed in addition to the processing of step S7 in FIG. 5 discussed above. More specifically, the controller 8 of the biological information measurement device charging device 1 displays messages such as "Charging and time setting complete," "Charging end time: 18:05:00," "Current time: 18:05:00," and "But no measurement for 10 minutes," as well as charging end information, time information, and measurement-impossible time information, on the display section 5 of the biological information measurement device charging device 1 (step S7 in FIG. 11).

Of course, the current time is updated.

The user can look at the display section 5 of the biological information measurement device charging device 1 and see that the charging of the biological information measurement device 2 and the setting of the time have finished.

After this, the controller 8 performs the procedure of step S8 in FIG. 11, just as with the procedure of step S8 in FIG. 5, and this series of charging processing is concluded.

Next, the operation of the biological information measurement device 2 during the charging of the biological information measurement device 2 and time setting will be described through reference to the flowchart in FIG. 12.

Figure 12:
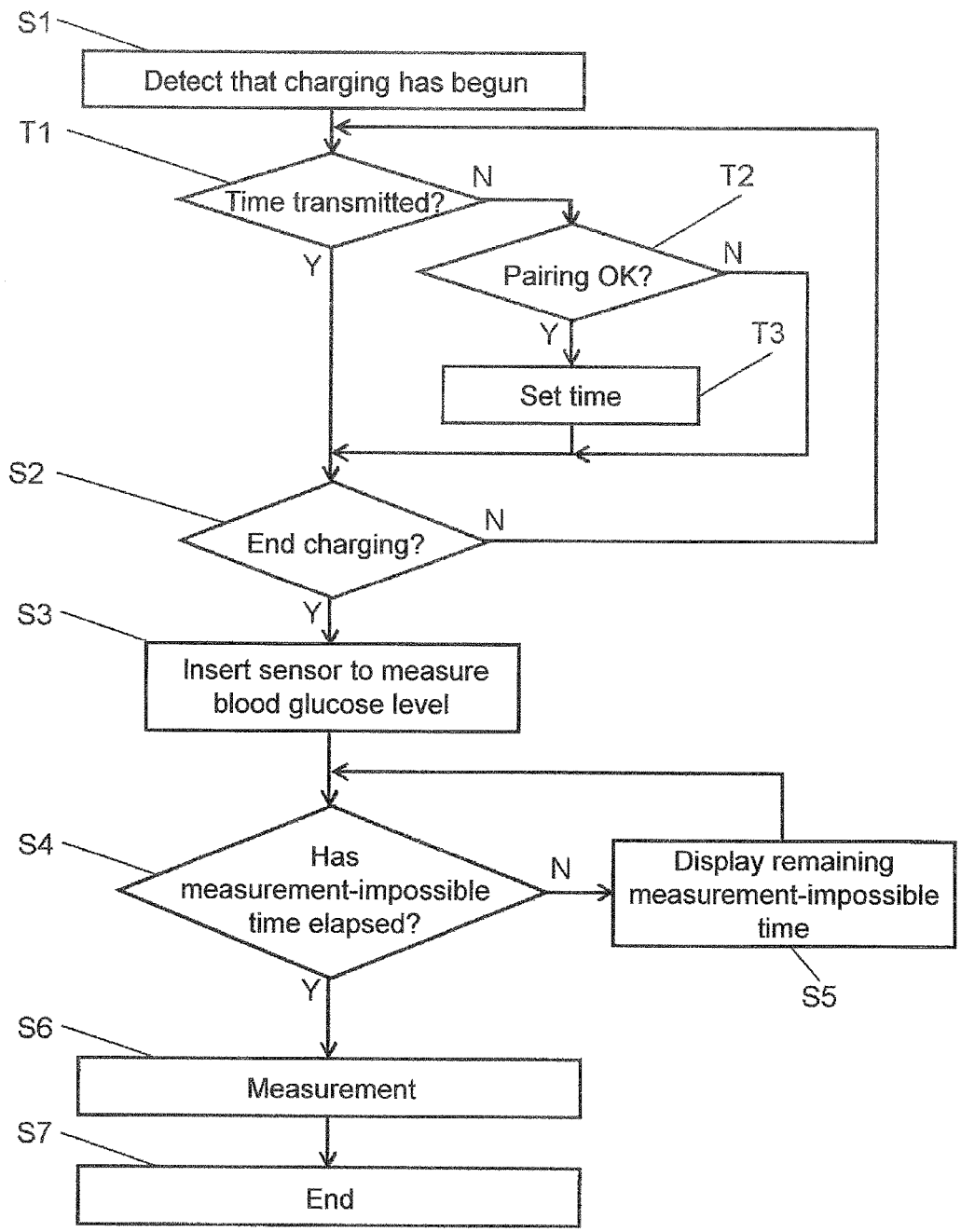
FIG. 12 is an operational flowchart of the biological information measurement device in the second embodiment of the present invention.

In FIG. 12, steps T1 to T3 are inserted as time setting processing in between steps S1 and S2 in the operational flowchart of FIG. 7.

In step S1 in FIG. 12, if the start of charging is detected, the controller 21 of the biological information measurement device 2 confirms whether or not time information has been received from the clock 10 of the biological information measurement device charging device 1 (step T1 in FIG. 12). This confirmation is determined by whether or not communication end information (such as a communication end flag) has been stored in the memory section 24. This communication end information is deleted in advance by the controller 21 when the start of charging is detected.

Immediately after the start of charging, the time information for the biological information measurement device charging device 1 has not yet been received by the biological information measurement device 2, so there is no communication end information. In view of this, the controller 21 pairs the receiver 28 of the biological information measurement device 2 with the transmitter 27 of the biological information measurement device charging device 1 in order to receive time information, and confirms whether or not communication is possible (step T2 in FIG. 10).

If the pairing is successful, the controller 21 receives time information (current time) from the clock 10 of the biological information measurement device charging device 1 via the transmitter 27 of the biological information measurement device charging device 1 and the receiver 28 of the biological information measurement device 2, and sets the clock 25.

Specifically, when the user merely places the biological information measurement device 2 on the contact face 4 of the biological information measurement device charging device 1, time information from the clock 10 of the biological information measurement device charging device 1 is set in the clock 25 of the biological information measurement device 2.

As a result, the clock 25 of the biological information measurement device 2 can be set to the precise time.

At this point, the controller 21 displays, for example, "Current time: 18:00:00" on the display section 14 of the biological information measurement device 2, and notifies the user that the reception of time information by the receiver 28 is complete. After this, the display is updated to match the time, and after a specific length of time (such as 30 seconds), the display is switched to indicate that charging is in progress, such as "Charging."

The controller 21 stores communication end information in the memory section 24 (step T3 in FIG. 12).

After this, step S2 in FIG. 12 is executed, and charging is continued.

In step S2 in FIG. 12, if the charging is not yet finished, the flow returns to step T1 in FIG. 12. This time, since time information of the biological information measurement device charging device 1 has been received in step T3 in FIG. 12, the flow returns to step S2 in FIG. 12 right away, and charging is continued.

In step T2 in FIG. 12, if pairing has failed, the controller 21 of the biological information measurement device 2 executes step S2 in FIG. 12 and continues charging, while the flow returns to step T2 in FIG. 12 via step T1 in FIG. 12, and the receiver 28 is paired with the transmitter 27 of the biological information measurement device charging device 1.

After charging is finished in step S2 in FIG. 12, that is, after the reception of time information by the receiver 28 is complete and charging of the rechargeable battery 22 is complete, the controller 21 displays messages such as "Charging end time: 18:05:00," "Current time: 18:05:00," and "No measurement for another 10 minutes," as well as charging end information, time information, and measurement-impossible time information, on the display section 14 of the biological information measurement device 2. Of course, the current time is updated.

The user can look at the display section 14 of the biological information measurement device 2 and see that charging has finished, and can also confirm that the current time has been precisely set. As a result, the biological information measurement device 2 can be used with confidence.

In order to reduce heat generated by the display section 14, the charging end information, the time information, and the measurement-impossible time information are displayed for a specific length of time with the brightness of the display section 14 reduced.

Once charging is finished, the measurement processing of steps S3 to S7 in FIG. 12 is carried out just as with the measurement processing of steps S3 to S7 in FIG. 7 discussed above.

As described above, in this embodiment the receiver 28 inside the main body case 13 of the biological information measurement device 2 is brought into contact with the contact face 4 of the biological information measurement device charging device 1, after which time information is received from the transmitter 27 of the biological information measurement device charging device 1. Accordingly, pairing and RFID communication can be reliably performed in a state in which the receiver 28 of the biological information measurement device 2 and the transmitter 27 of the biological information measurement device charging device 1 are in close proximity.

Furthermore, in this embodiment, as discussed above, one the time has been set for the biological information measurement device charging device 1, the controller 8 activates the operation of the charging start key 6, and preparation for charging is complete. That is, after the time setting is concluded for the biological information measurement device charging device 1, time setting and charging of the biological information measurement device 2 are performed, so the precise time of the biological information measurement device charging device 1 can be set to the clock 25 of the biological information measurement device 2 during charging.

As described above, in this embodiment the controller 8 of the biological information measurement device charging device 1 is connected to the clock 10 and the transmitter 27 that transmits time information from the clock 10 by radio waves, as shown in FIG. 9.

As shown in FIG. 10, the receiver 28, which receives by radio waves the time information sent by the transmitter 27 of the biological information measurement device charging device 1, is connected to the controller 21 of the biological information measurement device 2.

Specifically, when the user places the biological information measurement device 2 on the biological information measurement device charging device 1, the biological information measurement device 2 is charged by the biological information measurement device charging device 1. In addition, time information from the clock 10 of the biological information measurement device charging device 1 can be sent to the clock 25 of the biological information measurement device 2 via the receiver 28 during this charging.

Therefore, the clock 25 of the biological information measurement device 2 can be set to the precise time.

As a result, the clock 25 of the biological information measurement device 2 can be precisely set while the proper measurement can be performed.

As discussed above, the present invention includes a first main body case having a biological information measurement device contact face on its surface, a first non-contact charging portion disposed inside the first main body case and opposite the contact face, a first controller that is connected to this first non-contact charging portion, and a first display section that is connected to this first controller. The first controller displays on the first display section that the biological information measurement device will be incapable of measurement for a specific length of time after the end of charging of this biological information measurement device. This configuration allows the proper measurement to be performed by the biological information measurement device.

Specifically, with the present invention, it is displayed that the biological information measurement device will be incapable of measurement for a specific length of time (namely, until the temperature inside the biological information measurement device has naturally cooled to the temperature outside the biological information measurement device), so the user can see that the biological information measurement device is incapable of measurement.

When the biological information measurement device is then used after this display has disappeared, since the temperature inside the biological information measurement device by that point has naturally cooled to the same temperature as outside the biological information measurement device, the proper temperature correction can be performed.

As a result, the proper measurement can be performed.

INDUSTRIAL APPLICABILITY

The present invention is expected to find wide application as a biological information measurement device charging device, and as a biological information measurement device that is charged by this charging device.

The invention claimed is:

1. A biological information measurement device comprising:

a main body case including a sensor mounting portion to which a sensor for measuring a biological information is mounted;

a measurement section connected to the sensor mounting portion inside the main body case;

a controller connected to the measurement section;

a rechargeable battery connected to the controller;

a non-contact charging portion connected to the controller, the non-contact charging portion configured to charge the battery;

a clock connected to the controller, the clock configured to send measurement time of the measurement section;

a receiver connected to the controller, the receiver configured to receive time information of the clock via radio waves;

the controller sets the time information of the clock received via the receiver to the clock after start of charging the battery by the non-contact charging portion, and then continues charging of the battery, and a frequency of the non-contact charging portion used for charging the battery is different from a frequency of the receiver used for receiving the time information and wherein the controller confirms whether or not communication with a transmitter which send the time information is possible by pairing with the transmitter and the receiver after start of charging the battery, and the controller receives the time information from the transmitter when the pairing is successful, or the controller continues charging and performs pairing again when the pairing has failed.

2. The biological information measurement device according to claim 1, further comprising;

a display section connected to the controller;

wherein the controller displays a notice for notifying a user that a reception of time information by the receiver is complete on the display section when the time information is set on the clock, and then displays a display for indicating that charging is in progress on the display section.

3. The biological information measurement device according to claim 2, wherein:

the controller displays the charging completion information and the time information on the display section after an end of charging the battery.

* * * * *